(12) United States Patent
Bottomley et al.

(10) Patent No.: US 7,141,385 B2
(45) Date of Patent: **\*Nov. 28, 2006**

(54) MICROCANTILEVER APPARATUS AND METHODS FOR DETECTION OF ENZYMES, ENZYME SUBSTRATES, AND ENZYME EFFECTORS

(75) Inventors: Lawrence A. Bottomley, Lawrenceville, GA (US); Madhushree Ghosh, San Diego, CA (US); Shanxiang Shen, Bethesda, MD (US); Richard Saul, Gaithersburg, MD (US); Sebastian Kossek, Phoenix, AZ (US); Gary W. Pace, Winchester, MA (US)

(73) Assignee: Protiveris, Inc., Rockville, MD (US)

( * ) Notice: Subject to any disclaimer, the term of this patent is extended or adjusted under 35 U.S.C. 154(b) by 395 days.

This patent is subject to a terminal disclaimer.

(21) Appl. No.: 10/346,443

(22) Filed: Jan. 17, 2003

(65) Prior Publication Data

US 2004/0029108 A1    Feb. 12, 2004

Related U.S. Application Data

(63) Continuation-in-part of application No. 09/951,131, filed on Sep. 12, 2001.

(51) Int. Cl.
*G01N 33/573* (2006.01)
*G01N 33/542* (2006.01)
*G01N 21/00* (2006.01)
*G01N 21/29* (2006.01)
*G11N 33/53* (2006.01)

(52) U.S. Cl. .......... 435/7.4; 435/4; 435/7.71; 435/7.9; 435/176; 435/183; 435/288.7; 422/55; 422/57; 422/58; 422/82.05; 422/102; 422/104

(58) Field of Classification Search ........... 435/7.1, 435/7.4, 7.6, 7.71, 7.72, 16–28, 286.1, 287.1, 435/287.9, 288.4, 288.7; 436/518, 532, 536; 250/306; 206/290; 422/82.01
See application file for complete search history.

(56) References Cited

U.S. PATENT DOCUMENTS

| | | | |
|---|---|---|---|
| 3,741,876 A | * | 6/1973 | Guilbault .............. 435/10 |
| 3,977,944 A | * | 8/1976 | Muller-Matthesius et al. ............. 435/10 |
| 4,411,989 A | * | 10/1983 | Grow ................. 435/20 |
| 5,156,810 A | | 10/1992 | Ribi et al. ........ 422/82.01 |
| 5,445,008 A | | 8/1995 | Wachter et al. ...... 73/24.06 |
| 5,643,908 A | | 7/1997 | Sugimura et al. ...... 514/247 |
| 5,653,939 A | | 8/1997 | Hollis et al. .......... 522/50 |
| 5,668,734 A | * | 9/1997 | Krishna et al. ........ 702/22 |

(Continued)

FOREIGN PATENT DOCUMENTS

WO      WO 01/14823 A1     3/2001

OTHER PUBLICATIONS

Fang et al. (2000). *Proc. Natl. Acad. Sci.* 97, No. 8: 3884-3889.

(Continued)

*Primary Examiner*—Bao-Thuy L. Nguyen
*Assistant Examiner*—Unsu Jung
(74) *Attorney, Agent, or Firm*—Sonia K. Guterman; Lawson & Weitzen, LLP

(57) ABSTRACT

An apparatus and a method are provided for detecting an enzyme, or or for detecting a substrate of an enzyme or for detecting an enzyme effector such as an inhibitor, by measuring a change in deflection of a microcantilever having a substrate or an enzyme, respectively, attached to a surface of the microcantilever.

2 Claims, 4 Drawing Sheets

U.S. PATENT DOCUMENTS

| | | | | |
|---|---|---|---|---|
| 5,700,675 | A | * 12/1997 | Rubin et al. | 435/194 |
| 5,719,324 | A | 2/1998 | Thundat et al. | 73/24.01 |
| 5,763,768 | A | 6/1998 | Henderson et al. | 73/105 |
| 5,772,926 | A | * 6/1998 | Akhavan-Tafti | 252/700 |
| 5,807,688 | A | 9/1998 | Blackburn et al. | 435/7.6 |
| 5,807,758 | A | 9/1998 | Lee et al. | 436/526 |
| 5,814,525 | A | 9/1998 | Renschler et al. | 436/524 |
| 5,827,712 | A | 10/1998 | Yokoyama et al. | 435/193 |
| 5,908,960 | A | 6/1999 | Newlander | 564/177 |
| 5,923,421 | A | 7/1999 | Rajic et al. | 356/328 |
| 5,981,297 | A | 11/1999 | Baselt | 436/514 |
| 5,985,630 | A | * 11/1999 | Hawkes | 435/184 |
| 5,992,226 | A | 11/1999 | Green et al. | 73/105 |
| 6,016,686 | A | 1/2000 | Thundat | 73/23.2 |
| 6,037,361 | A | 3/2000 | Roth et al. | 514/411 |
| 6,041,642 | A | 3/2000 | Duncan | 73/24.01 |
| 6,050,722 | A | 4/2000 | Thundat et al. | 374/121 |
| 6,096,559 | A | 8/2000 | Thundat et al. | 436/147 |
| 6,107,000 | A | 8/2000 | Lee et al. | 430/296 |
| 6,118,124 | A | 9/2000 | Thundat et al. | 250/332 |
| 6,123,819 | A | 9/2000 | Peeters | 204/403 |
| 6,159,746 | A | * 12/2000 | Islam et al. | 436/518 |
| 6,180,381 | B1 | 1/2001 | Montgomery et al. | 435/196 |
| 6,210,667 | B1 | 4/2001 | Reed | 424/94.64 |
| 6,258,555 | B1 | 7/2001 | Burnham et al. | 435/43 |
| 6,271,235 | B1 | 8/2001 | Dressman et al. | 514/255 |
| 6,289,717 | B1 | 9/2001 | Thundat et al. | 422/82.01 |
| 6,377,895 | B1 | 4/2002 | Horlbeck | 702/22 |
| 6,429,302 | B1 | * 8/2002 | Kennedy | 536/23.5 |
| 2002/0072127 | A1 | * 6/2002 | Sofield et al. | 436/518 |
| 2003/0013185 | A1 | * 1/2003 | Saraf | 435/287.2 |
| 2003/0165488 | A1 | * 9/2003 | Kletzien et al. | 424/94.63 |

OTHER PUBLICATIONS

Gen. Engin. News 23(1), Jan. 1, 2003.

Ilic et al. (2000). *Appl. Phys. Lett.* 77, No. 3: 450-452.

"Impact-CN System: Recombinant FusionProtein Expression And One-Step Affinity Purification," *New England Biolabs Catalog.* 142-143 (2000-2001).

Thundat et al. (1997). *Microscal Thermophysicial Engineering.* 1:185-199.

Wu, et al (2001). *Nature Biotechnology.* 19:856-860.

\* cited by examiner

MICROCANTILEVER APPARATUS AND METHODS FOR DETECTION OF ENZYMES, ENZYME SUBSTRATES, AND ENZYME EFFECTORS

RELATED APPLICATIONS

This application is a continuation-in-part of and claims priority in part from U.S. application Ser. No. 09/951,131, filed in the U.S. Patent and Trademark Office on Sep. 12, 2001, and which is hereby incorporated herein in its entirety.

TECHNICAL FIELD

The general field of the invention relates to an apparatus and a method for detecting the presence of an enzyme in a sample by measuring a deflection of a microcantilever, the surface of the microcantilever having a substrate for the enzyme. In various embodiments, the invention is of use in proteomics, drug discovery, medical research, medical, veterinary, dental diagnostics, forensics, and military applications.

BACKGROUND

A large variety of enzymes are important in medicine, industry, and other applications. Discovery of novel enzymes has gone hand-in-hand with development of certain industries, for example the discovery of bacterial restriction enzymes and the development of genetic engineering. Enzymes are important in various medical pathologies (Fang J., et al., Proc. Natl. Acad. Sci. U.S. 97: 3884–3889, 2000), as novel therapeutics (U.S. Pat. No. 6,210,667 issued Apr. 3, 2001), as targets for development of novel therapeutic agents, for example, HIV protease (U.S. Pat. No. 6,271,235 issued Aug. 7, 2001), in industrial processes such as antibiotic biosynthesis (U.S. Pat. No. 6,258,555 issued Jul. 10, 2001), degradation of unwanted materials such as polyurethane (U.S. Pat. No. 6,180,381, issued Jan. 30, 2001) and in the food industry (U.S. Pat. No. 5,827,712, issued Oct. 27, 1998). The need to obtain novel enzyme activities is so great that protein engineering research has been directed toward development of catalytic antibodies (U.S. Pat. No. 5,807,688, issued Sep. 15, 1998).

Thin bimorph microcantilevers can undergo bending (deflection) due to differential stresses following exposure to and binding of a compound from their environment, for example in a fluid sample. Soft microcantilevers having spring constants less than 0.1 N/m are sensitive to stress differentials that arise as a result of interactions between extremely small amounts of a substrate material on a surface of the microcantilever and one or more materials in a sample. For a given microcantilever with a specially designed coating layer, the deflection yields information about components of the environment to which the microcantilever is exposed. Microcantilevers are capable of detecting calorimetric enzyme-mediated catalytic biological reactions with femtoJoule resolution. (Thundat et al., "Microcantilever Sensors", Microscale Thermophysical Engr. 1, pgs. 185–199, 1997.) Oligonucleotide interactions within a sample can be detected using a monolithic array of test sites formed on a surface to which the sample is applied (U.S. Pat. No. 5,653,939).

There is a need for methods and an apparatus for detecting an interaction between an enzyme and its enzymatic substrate, for detecting a protein having an enzymatic activity or a related molecule, such as a catalytic antibody, or a binding or associating protein, as measured by a response of a microcantilever to a stress caused by changes in free surface energy and bonding energy. There is a need in medical and veterinary diagnostics, and in research, for detection and analysis of binding and activities of enzymes and enzyme-like proteins.

SUMMARY

The invention in one embodiment provides a method for detecting an enzyme, the method comprising: depositing a coating material on a first surface of at least one microcantilever; adding at least one substrate to the coating material, the substrate capable of interacting with the enzyme; exposing the microcantilever with the substrate to a sample; and measuring a deflection of the microcantilever, wherein the deflection indicates the presence of the enzyme in the sample. In a related embodiment, adding the substrate comprises adding at least one biomaterial, a biomaterial selected from the group consisting of a nucleic acid, a protein, a lipid, a hydrocarbon, and a polysaccharide, for example. In another related embodiment, the substrate is a drug.

In a related embodiment of this method, the deflection is caused by a change in stress on the surface of the microcantilever. In a preferred embodiment, the deflection is measured by observing the change by an optical means, which preferably includes a laser. Alternatively, an electron tunneling means, a capacitive means, a piezoelectric means or a piezoresistive means may be used to observe the change in deflection.

In a related embodiment, the method further comprises analyzing the deflection of the microcantilever as a function of a time parameter determined from the time of exposing the microcantilever to the sample. Analyzing the deflection comprises using a microprocessor adapted for comparing, calculating, and storing the deflection of the microcantilever as a function of a time parameter. Analyzing the deflection further comprises analyzing a parameter selected from the group of: concentration of enzyme, concentration of substrate, presence of a cofactor and presence of an inhibitor.

In a related embodiment, the method comprises the microcantilever having a length that is at least about 20 µm, at least about 20 µm to about 150 µm, the length is for example about 50 µm to about 250 µm, about 100 µm to about 400 µm, about 200 µm to about 500 µm, or about 250 µm to about 750 µm. Further, the width can be at least about 5 µm to about 20 µm, about 10 µm to about 30 µm, about 20 µm to about 50 µm, about 25 µm to about 100 µm, or to about 300 µm. The height can be at least about 0.1 µm, for example, at least about 0.4 µm, about 4 µm to about 10 µm. Depositing the coating material further comprises depositing a metal. The metal is selected from at least one of the group consisting of aluminum, copper, gold, chromium, titanium, and silver. For example, the metal is gold.

In a related embodiment, the method further comprises depositing a plurality of metals. Depositing a plurality of metals further comprises depositing a first layer of chromium and a second layer of gold. In a related embodiment, the method further comprises depositing a first layer of titanium and a second layer of gold. The metal in other embodiments is an amalgam or an alloy.

In a related embodiment, the microcantilever has a second surface selected from the group consisting of aluminum oxide, iridium oxide, silicon, silicon oxide, silicon nitride, tantalum pentoxide, and a plastic polymer.

In a related embodiment of the invention provides at least one microcantilever which is a block array having a plurality of microcantilevers.

In a related embodiment, the method further comprises, prior to adding the substrate to the first surface, reacting the microcantilever with a bifunctional cross-linker, the bifunctional cross-linker capable of further reacting with the substrate. The bifunctional cross-linker is selected from the group consisting of: dithiobis(succinimido undecanoate (DSU); long chain succinimido-6-[3-(2-pyridyldithio)-propionamido] hexanoate (LCSPDP); succinimidyl-6-[3-(2-pyridyldithio)-propionamido] hexanoate (SPDP); and m-maleimidobenzoyl-N-hydroxysuccinimide ester. For example, the bifunctional cross-linker is DSU.

In a related embodiment of the method, the microcantilever detects an enzyme selected from the group consisting of: a hydrolase, an oxidoreductase, a transferase, a lyase, and a ligase. For example, the enzyme is a hydrolase. The hydrolase is a protease. For example, the protease is a metalloprotease or a serine protease. Further, the enzyme is selected from the group of consisting of: a kinase, a phosphatase, an endopeptidase, an exopeptidase, a restriction endonuclease, an exonuclease, and a polymerase.

The transferase is selected from the group consisting of: a glycosyl transferase, a glutathione S-transferase, an acetyl transferase, and a DNA methyl transferase. For example, the lyase is selected from the group consisting of: a polysaccharide lyase, a 3-hydroxy-3-methylglutaryl CoA lyase, an arginiosuccinate lyase and an isocitrate lyase. For example, the oxidoreductase is selected from the group consisting of: a hydroxylamine oxidoreductase, a glyphosphate oxidoreductase, a quinine oxidoreductase, a ubiquinone oxidoreductase, and a protein disulfide oxidoreductase. In a related embodiment of the invention, the sample comprises an enzyme that is substantially purified. According to a further embodiment of the method, the sample comprises a biological fluid. The biological fluid is selected from the group consisting of: a cell lysate, a culture medium, a spent medium, an animal extract, and a plant extract. For example, the biological fluid comprises a bodily fluid from a vertebrate animal, such as a human or other mammal. According to an embodiment provided by this method, the bodily fluid is selected from the group consisting of: blood, lymph, tissue fluid, urine, bile, sweat, synovial fluid, amniotic fluid, abdominal fluid, pericardial fluid, pleural fluid, cerebrospinal fluid, gastric juice, intestinal juice, joint cavity fluid, tears, and nasal discharge.

In a related embodiment of the invention, the enzyme is associated with a medical condition in a vertebrate animal. The medical condition is a genetic defect for example, the medical condition is selected from the group consisting of: Fabry disease, Gaucher disease, Lesch-Nyhan disease, Tay-Sachs disease, mannosidosis disease, X-linked glomerular disease, and mucopolysaccharidosis. In another embodiment, the medical condition is a cancer, for example, the cancer is selected from a cancer of the brain, liver, pancreas, lung, prostate, or breast. In a related embodiment, the cancer is prostate, and the enzyme is prostate specific antigen. In a related embodiment, the cancer is breast cancer, and the enzyme is a collagenase. The medical condition in another embodiment is the presence of an infectious agent. For example, the infectious agent is selected from the group consisting of: a virus, a bacterium, a fungus, a protozoan, and a helminth.

An embodiment of the invention provides a method for detecting in a sample an associating substance that binds to a substrate, wherein detecting the substance involves at least one microcantilever configured to be responsive to a microforce, the method comprising: depositing a coating material on a first surface of the microcantilever; adding at least one substrate to the coating material, the substrate capable of interaction with the substance; exposing the microcantilever with the substrate to the sample; and measuring a resulting free surface energy change on the surface of the microcantilever, wherein the surface energy change indicates binding to the substrate by the associating substance in the sample.

In a related embodiment of the invention, the associating substance is selected from the group consisting of: a binding protein, an enzyme, a cofactor, an antibody, a polysaccharide, a lipid, a nucleic acid, and a steroid. For example, the associating substance is an enzyme wherein the enzyme binds the substrate and fails to dissociate. In another example, the enzyme has no activity on the substrate. In yet another example, the substrate is a non-cleavable pseudosubstrate.

The substrate in a related embodiment is a plurality of biomaterials. The substrate in another related embodiment comprises an inhibitor of enzymatic activity.

In another embodiment, the invention provides a method of screening for an inhibitor of an enzyme, wherein detecting the inhibitor involves having a substrate for the enzyme on a microcantilever, the method comprising: adding the substrate to a first side of a first microcantilever having a coating, the substrate capable of interacting with the enzyme and with the coating; exposing the first microcantilever with the substrate to a sample, the sample containing a candidate inhibitor and the enzyme; and measuring a deflection of the first microcantilever in comparison to a deflection of a second microcantilever exposed to the enzyme in the absence of the candidate inhibitor. In a related embodiment of the method, the first microcantilever and the second microcantilever are located in a first interaction cell and a second interaction cell of a microfluidics device. In a related embodiment, a third microcantilever and a fourth microcantilever are located in a third interaction cell and a fourth interaction cell, the third cell and fourth cell having different concentrations of enzyme than the first cell and the second cell. In a related embodiment, a third microcantilever and a fourth microcantilever are located in a third and fourth interaction cell, the third cell and the fourth cell having different samples of candidate inhibitors than the first cell and the second cell.

An embodiment of the invention provides an apparatus to measure a microforce generated by an interaction between an enzyme and a biomaterial, comprising: at least one microcantilever, wherein the microcantilever has a length, a width, and a thickness; a coating material deposited on a first surface of the microcantilever; a biomaterial capable of attachment to the coating material; and at least one interaction cell, wherein the microcantilever with the coating material and the biomaterial is exposed to a sample, the sample comprising the enzyme. The biomaterial comprises an enzymatic substrate. Alternatively, the biomaterial comprises an enzymatic pseudosubstrate. The microcantilever in certain embodiments comprises a block array having a plurality of microcantilevers. The microcantilever has dimensions that are microscopic, having a length that is at least about 20 µm to about 750 µm, a width that is at least about 5 µm to about 300 µm, and a height that is at least about 0.1 µm to about 10 µm. The microcantilever coating is selected from at least one of the group consisting of copper, gold, aluminum, chromium, titanium, and silver. For example, the coating is gold coating. According to a further embodiment of this apparatus, a second surface of the microcantilever is selected from the group consisting of silicon, silicon nitride, other silicon compounds, metal compounds, gallium arsenide, germanium, germanium dioxide, glass, zinc oxide, diamond, quartz, palladium and a plastic polymer. The apparatus in one embodiment is disposable. In another embodiment, the apparatus is reusable.

A feature of the present invention is an apparatus to measure a microforce generated by an interaction between an enzymatic substrate and an enzyme, the apparatus comprising: at least one microcantilever, wherein the microcantilever has a length, a width, and a thickness; a coating material deposited on a first surface of the microcantilever; an enzyme bound to the coating material; and at least one interaction cell, wherein a presence of the microforce is indicated by deflection of the microcantilever due ro the presence in the sample of the substrate.

An embodiment of the invention is an apparatus that further comprises a second microcantilever in a second interaction cell for receiving a second sample. For example, the second interaction cell contains a potential inhibitor of binding of the enzyme to the substrate. The inhibitor can be a competitive inhibitor. For example, the competitive inhibitor is an elutant (eluting agent) having greater affinity for the enzyme than the substrate. Alternatively, the the second interaction cell contains a potential inhibitor of binding of the enzyme which is a competitive inhibitor. In another embodiment, the substrate is a pseudo-substrate. The interaction cell with the microcantilever can be housed in a microfluidics device for receiving a sample.

Another aspect of the present invention is an apparatus to measure a microforce generated by an interaction between a protein and an effector of the protein, the apparatus comprising: at least one microcantilever, wherein the microcantilever has a length, a width, and a thickness; a coating material deposited on a first surface of the microcantilever, the protein attached to the coating material; and at least one interaction cell, wherein the interaction cell with the microcantilever is housed in a microfluidics device for receiving a sample, and detection of the microforce is indicated by deflection of the microcantilever due ro the presence in the sample of the effector. As used herein and in the claims, the term "effector" means a molecule that is capable of altering an activity of the protein, for example, the effector can be a substrate, an inhibitor of either an enzymatic activity or an affinity of the enzyme for binding to a substrate, or the effector is an activator or an actuator of an enzymatic activity or of affinity of binding by the enzyme to substrate. The protein in some embodiments is an enzyme.

Further, the at least one microcantilever and the at least one interaction cell are a first microcantilever in a first interaction cell and a second microcantilever in a second interaction cell. The second interaction cell can contain an candidate effector and the first interaction cell can lack the candidate effector.

Yet another embodiment of the invention is an apparatus to measure a microforce generated by an interaction between an enzyme and a biomaterial, the apparatus comprising at least one microcantilever, wherein the microcantilever has a length, a width, and a thickness; a coating material deposited on a first surface of the microcantilever, the enzyme attached to the coating material; and at least one interaction cell containing the microcantilever, wherein the interaction cell with the microcantilever is housed in a microfluidics device for receiving a sample, and detection of the microforce is indicated by deflection of the microcantilever due to the presence in the sample of the biomaterial. The biomaterial comprises for example an enzymatic substrate. Alternatively, the biomaterial comprises an enzymatic pseudosubstrate. The at least one microcantilever further comprises a block array having a plurality of microcantilevers.

With respect to the above embodiments of an apparatus herein, the microcantilever length is about 250 µm to about 750 µm, the width is about 20 µm to about 300 µm, and the thickness is about 0.1 µm to about 10 µm. The coating material is selected from at least one of the group consisting of copper, gold, aluminum, chromium, titanium, and silver. In a preferred embodiment, the coating material is gold. A second surface of the microcantilever is selected from the group consisting of silicon, silicon nitride, other silicon compounds, metal compounds, gallium arsenide, germanium, germanium dioxide, glass, zinc oxide, diamond, quartz, palladium and a plastic polymer. The apparatus is disposable. Alternatively, the apparatus is reusable. The apparatus can further comprise at least a second microcantilever in a second interaction cell for receiving a second sample.

Yet another embodiment of the invention herein is an apparatus to identify an inhibitor of a microforce generated by an interaction between an enzymatic substrate and an enzyme, comprising: at least one microcantilever, wherein the microcantilever has a length, a width, and a thickness; a coating material deposited on a first surface of the microcantilever; the enzyme attached to the microcantilever by covalent binding to the coating material; and at least one interaction cell, wherein the interaction cell with the microcantilever is housed in a microfluidics device for receiving a sample containing a potential inhibitor, and detection of the inhibitor of the microforce is indicated by an altered deflection of the microcantilever due ro the presence in the sample of the inhibitor, compared to in the absence of the inhibitor. The apparatus can further comprise a second microcantilever in a second interaction cell for receiving a second sample.

A feature of the invention is a method for identifying an inhibitor of an enzyme from among a plurality of potential inhibitors of binding of the enzyme to a substrate, the method comprising: adding a sample of one of the potential inhibitors with the substrate to a first interaction cell in a microfluidics apparatus, the first interaction cell containing the enzyme bound to a surface of a first microcantilever; and, comparing a deflection of the first microcantilever in the first interaction cell to that of a second microcantilever in a second interaction cell, wherein the first and second microcantilevers are identically configured with enzyme bound to the surface, and the first and second interaction cells are identically configured to contain substrate, with the exception that the second cell does not receive a sample of the potential inhibitor, such a decrease in deflection of the first microcantilever in comparison to the second microcantilever is an indication that the inhibitor has been identified. The substrate can be a pseudosubstrate. The method in most embodiments further comprises using a third interaction cell containing a third microcantilever identically configured with enzyme bound to the surface. The third interaction cell receives for example an inhibitor that is a positive control which inhibits binding of substrate to the enzyme. Alternatively, the third interaction cell receives a control buffer lacking substrate.

Another embodiment of the invention is a method for identifying an elutant of a protein bound to an associating substance from among a plurality of candidate elutants, wherein the protein is attached to a surface of a first microcantilever in a first interaction cell and a second microcantilever in a second interaction cell, and wherein the protein is bound to the associating substance under nonenzymatic conditions, the method comprising: adding a sample of at least one of the candidate elutants to the first interaction cell; and comparing the deflection of the first microcantilever to that of the second microcantilever identically configured except for the absence of the candidate, such that a return to a base-line position of deflection of the first microcantilever compared to the second microcantilever indicates that the composition is an elutant. The method can further comprise comparing deflection of the first microcantilever to that of a third microcantilever in a third interaction cell, wherein the third interaction cell contains a microcantilever identically configured with associating substance, however in the absence of bound protein, such that the position of deflection of the third microcantilever is an indication of a base-line position. The method can further comprise comparing deflection of the first microcantilever to that of a third microcantilever in a third interaction cell, wherein the third interaction cell contains a microcantilever identically configured with associating substance, however in the presence of a different concentration of the candidate elutant.

In yet another embodiment, the invention features a method of screening a library of a plurality of candidate inhibitors to identify an inhibitor of an enzyme immobilized on a microcantilever, the method comprising: binding the enzyme to a first side of each of a first microcantilever and a second microcantilever, the enzyme binding the substrate absent an inhibitor; exposing the first microcantilever with the enzyme to a sample of a candidate inhibitor; and measuring a deflection of the first microcantilever in comparison to a deflection of the second microcantilever identically exposed to the substrate except in the absence of the candidate inhibitor, wherein an altered pattern of deflection of the first microcantilever compared to the second microcantilever identifies the inhibitor. Accordingly, the first microcantilever is located in a first interaction cell and the second microcantilever is located in a second interaction cell of a microfluidics device. A third microcantilever located in a third interaction cell and a fourth microcantilever located in a fourth interaction cell are exposed to a different concentration of the candidate than the first cell. Alternatively, a third microcantilever located in a third interaction cell and a fourth microcantilever located in a fourth interaction cell are exposed to different candidate inhibitors than the candidate in the first interaction cell.

DESCRIPTION OF SPECIFIC EMBODIMENTS

Figure 1:
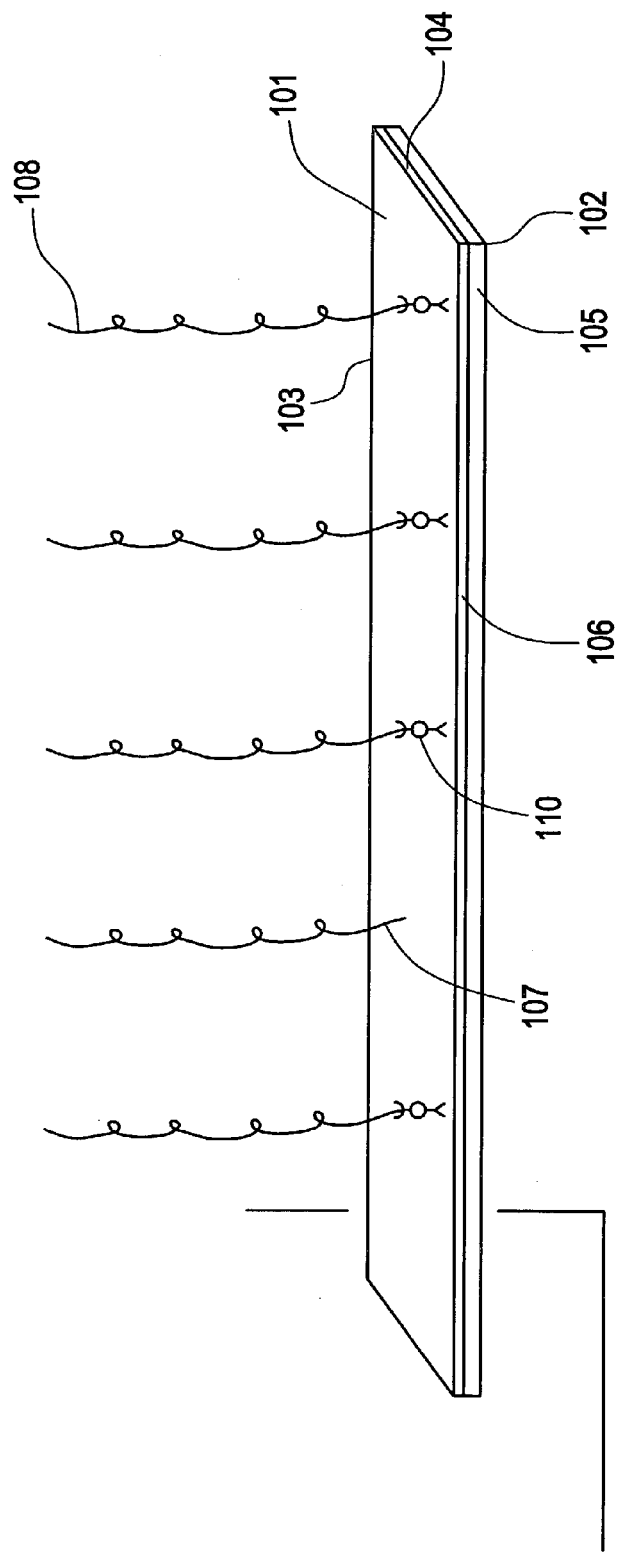
FIG. 1 is a schematic representation of a partial top view of a microcantilever showing three dimensions, first and second surfaces, and substrate molecules deposited on the first surface.

FIG. 1 shows a microcantilever having a first surface 101, a second surface 105, a height 102, a width 104, and a length 103. The first surface can have at least one coating 106. An enzymatic substrate 108 is affixed to the first surface directly 107, or by covalent reaction with a bifunctional cross-linking agent 110. Non-covalently bound substrate molecules can be washed from the first surface following a reaction with the cross-linking agent, for example by use of a buffer having a low pH, or a mild detergent. Covalent linking of substrate molecules, rather than direct binding, is a preferred embodiment, as the former process produces a more geometrically homogeneous array of substrate molecules.

Substrate molecules for enzymatic binding that are affixed to the microcantilever can be macromolecules, or can be low molecular weight molecules. Typical low molecular weight substrates for enzymes can have a size range of from about 100 to about 500, 200 to about 1,000, 500 to about 2,000, or about 1,000 to about 6,000 molecular weight. These substrates are exemplified by mono- or oligo-shccharides, -peptides, -nucleotides, and by nucleotide-mono-, di- and tri-phosphates, or by related pseudosubstrates that can be reversibly or irreversibly bound by the enzyme and are not cleaved or acted upon enzymatically.

Figure 2A:
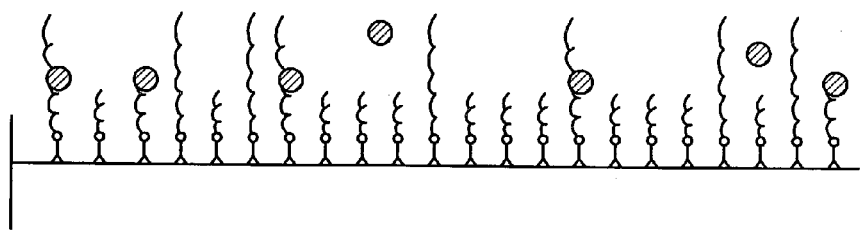
FIG. 2 is a schematic diagram of a side view of a microcantilever having molecules of a bifunctional cross-linking agent attached to the surface of the microcantilever and to a biomaterial, and the biomaterial bound directly to the surface of the microcantilever. Various types of enzymes and modes of binding to and digesting substrate molecules are shown.
Figure 2B:
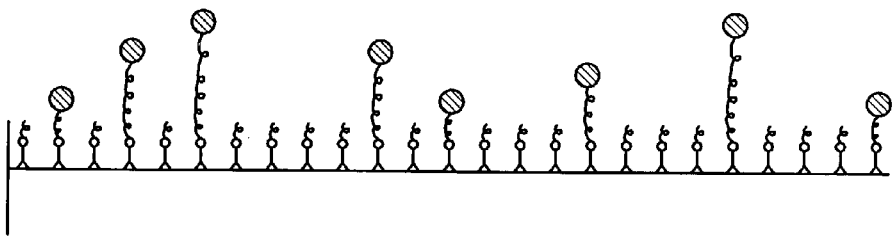
Figure 2C:
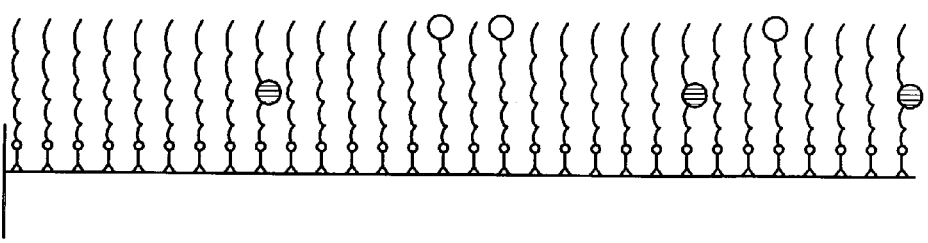

FIG. 2 illustrates the interaction of classes of enzymes with substrate molecules on a first surface of a microcantilever, following addition of an enzyme sample to the microcantilever. Prior to addition of sample, all substrate molecules are full-length, as shown in Panel A, second substrate molecule from right. Panel A shows an enzyme as a cross-hatched circle, binding to a recognition site on the interior of the substrate molecule (substrate molecule at left), and cleaving the substrate molecule, leaving a shorter product covalently attached to the surface (second, third, fifth, seventh, etc., substrate molecules from left). This result would be obtained from digestion of a DNA substrate molecule by an endonuclease such as a restriction enzyme, e.g., BamH1 or EcoR1, or from digestion of a protein substrate molecule by a protease such as trypsin. Panel B shows an enzyme as a cross-hatched circle, binding to a free end of a substrate molecule distal from the attached end, and cleaving the substrate processively. This result would be obtained from digestion of a nucleic acid or a protein substrate molecule by, for example, an exonuclease or an exopeptidase, respectively. Panel C shows interaction of binding proteins (open or stippled circles), or inactive enzymes, with substrate molecules. Following binding, no digestion of substrate molecules is obtained.

Figure 3:
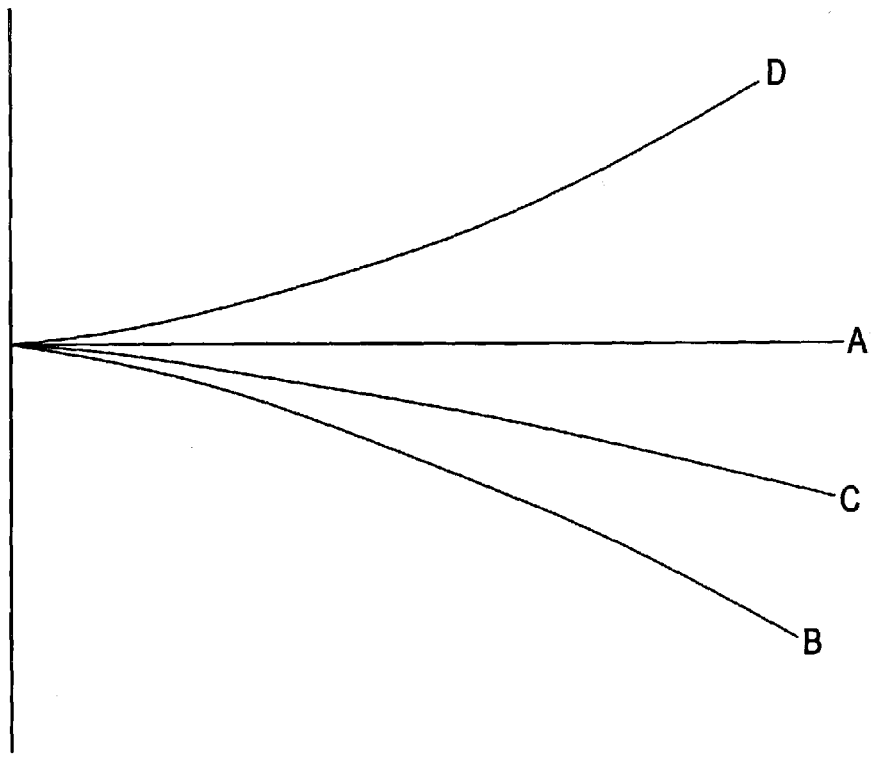
FIG. 3 is a schematic view of a microcantilever showing various potential positions of deflection and return to an original position.

FIG. 3 shows deflection of a microcantilever from an initial position, A. Addition of substrate molecules to a first surface can alter the position of the microcantilever to a new position, e.g., position B or position C. Subsequent enzyme digestion as in FIG. 2, panel A, or FIG. 2, panel B, can further alter the deflection, e.g., from position B to position D or from position C to position A. Binding of inactive enzyme or of a binding protein to the substrate can alter the position oft he microcantilever, causing deflection, for example, from position C to position B.

In an alternative embodiment, molecules of an enzyme are immobilized to a microcantilever, for the purpose of detecting a substrate or an effector, inhibitor, antibody, binding protein or other associating substance, to be identified in a sample from an environment. In yet another alternative, a protein lacking enzymatic activity is bound to a microcantilever. According to this embodiment, a microcantilever configured as shown in FIG. 4, having covalently bound an antibody which is a substrate for a protease, can also be used to detect other agents in a sample, for example, a general antibody-binding agent such as protein A from a bacterial species such as a *Staphylococcus aureus*; a low molecular weight molecule capable of binding to an antibody such as a mercuric ion; or a cognate antigen, such as a macromolecule for example a protein, or a low molecular weight epitope such as a heptapeptide.

Figure 4:
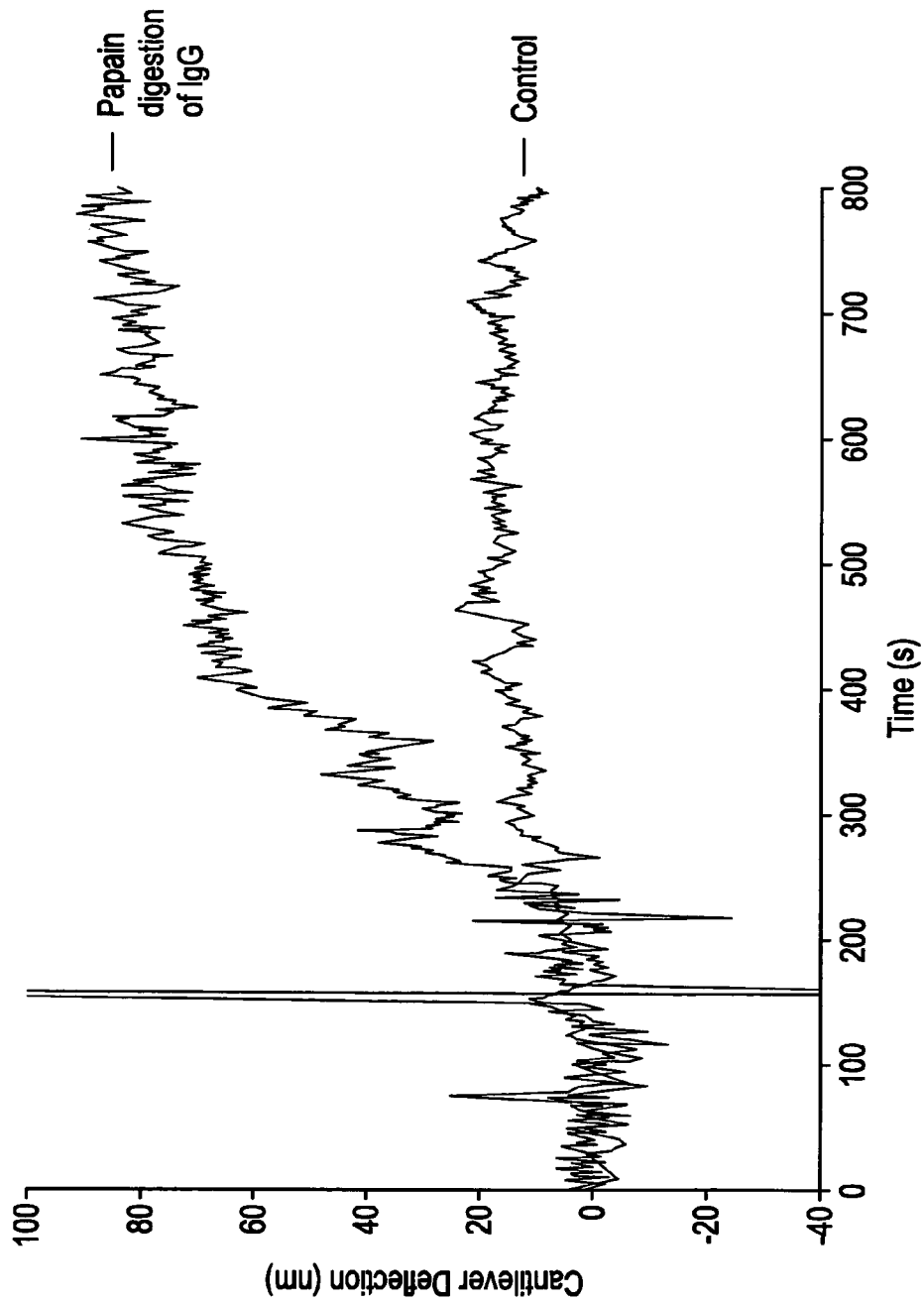
FIG. 4 is a time course (in seconds, on the abscissa) of microcantilever deflection (in nm, on the ordinate) as a result of papain digestion of IgG (upper function), compared to a prior control using the same microcantilever exposed to buffer only (lower function).

FIG. 4 shows a time course of deflection of a microcantilever, the first surface of which has been covalently attached to a protein substrate, a solution of IgG antibody molecules. The microcantilever having covalently attached antibody is first exposed to a control buffer (lower function), as a result of which exposure no change is observed in the deflection. The same microcantilever is then exposed to an appropriate concentration of the protease papain, as described in Example 1. The data show a significant change in deflection, of about 60 nm, occurring over a time course of several minutes following exposure to the papain.

Definitions

Unless the context otherwise requires, as used in this description and in the following claims, the terms below shall have the meanings as set forth below.

The term "microcantilever" is a structural term that refers to a flexible beam that may be bar-shaped, V-shaped, or have other shapes, depending on its application. One end of the microcantilever is fixed on a supporting base, another end standing freely. Microcantilevers are usually of microscopic dimensions, for example, the length can be at least about 50 µm to about 150 µm, about 50 µm to about 250 µm, about 100 µm to about 400 µm, about 200 µm to about 500 µm, or about 250 µm to about 750 µm. Further, the width can be at least about 5 µm, for example from about 5 µm to about 20 µm, from about 0 µm to about 30 µm, about 20 µm to about 50 µm, or about 25 µm to about 100 µm or to about 300 µm. The height can be about 0.1 µm, for example, from about 0.1 µm to about 0.4 µm, or to about 4 µm or to about 10 µm. Silicon and silicon nitride are the most common molecules used to fabricate microcantilevers. Other molecules have also been reported for making microcantilevers, including piezoelectric molecules, plastic molecules and various metals.

Specifically, microcantilevers can be manufactured from a variety of materials, including for example, ceramics, silicon, silicon nitride, other silicon compounds, metal compounds, gallium arsenide, germanium, germanium dioxide, zinc oxide, diamond, quartz, palladium, tantalum pentoxide, and plastic polymers. Plastics can include: polystyrene, polyimide, epoxy, polynorbornene, polycyclobutene, polymethyl methacrylate, polycarbonate, polyvinylidene fluoride, polytetrafluoroethylene, polyphenylene ether, polyethylene terephthalate, polyethylene naphthalate, polypyrrole, and polythiophene. Microcantilevers that are custom fabricated can be obtained for example from a manufacturer such as Diffraction Ltd., Waitsfield, Vt.

Microcantilevers with a compound immobilized on the surface on the free end have been used to detect and screen receptor/ligand interactions, antibody/antigen interactions and nucleic acid interactions (U.S. Pat. No. 5,992,226, issued on Nov. 30, 1999). Deflection is measured using optical and piezoelectric methods. Microcantilevers can measure concentrations using electrical methods to detect phase difference signals that can be matched with natural resonant frequencies (U.S. Pat. No. 6,041,642, issued Mar. 28, 2000.) Determining a concentration of a target species using a change in resonant properties of a microcantilever on which a known molecule is disposed, for example, a macromolecular biomolecule such as DNA, RNA, and protein, is described in U.S. Pat. No. 5,763,768.

A method and apparatus for detecting and measuring physical and chemical parameters in a sample media uses micromechanical potentiometric sensors (U.S. Pat. No. 6,016,686, issued Jan. 25, 2000). Detection of a chemical analyte is described in U.S. Pat. No. 5,923,421, issued Jul. 13, 1999. Magnetic and electrical monitoring of radioimmune assays, using antibodies specific for target species which cause microcantilever deflection, e.g., magnetic beads binding the target to the microcantilever, are described in U.S. Pat. No. 5,807,758, issued Sep. 15, 1998.

The term "first surface" as used herein refers to that geometric surface of a microcantilever designed to receive and bind to molecules of a substrate for an enzyme. One or more coatings can be deposited upon this first surface. Thus the term "second surface" refers to the area of the opposite side of the microcantilever which is designed not to contain coating or enzyme substrates. As the second surface is generally not coated, it is generally comprised of the material from which the microcantilever or microcantilever array is fabricated, prior to any coating procedure applied to the first surface. Alternatively, it may be coated with a material different from the first surface's coating.

A first surface of a microcantilever can be fabricated to have an intermediate layer, for example, sandwiched between the first surface comprising for example, gold, and the second surface, comprising for example silicon nitride. The intermediate layer may be an alloy comprising a plurality of metals, for example, the intermediate layer may be an amalgam comprising mercury with at least one of chromium, silver, and titanium. While mercury is not generally compatible with an environment having proteins such as enzymes, in some embodiments the amalgam or alloy of a middle layer may comprise mercury.

U.S. Pat. Nos. 6,096,559 issued Aug. 1, 2000, and 6,050,722 issued Apr. 18, 2000, describe fabrication of a microcantilever, including use of material such as ceramics, plastic polymers, quartz, silicon nitride, silicon, silicon oxide, aluminum oxide, tantalum pentoxide, germanium, germanium dioxide, gallium arsenide, zinc oxide, and silicon compounds. Coating of micromechanical sensors with various interactive molecules is described in U.S. Pat. No. 6,118,124, issued Sep. 12, 2000.

Deflection or bending of a microcantilever from a first position to at least a second position may be due to differential stress on a first surface of the microcantilever in comparison to a second surface, the change in surface stress resulting from exposure of the microcantilever to a component of a particular environment. A microcantilever can deflect following a change from a first environment to a second environment. For example, the environment can be altered in many possible ways including: an enzyme can be added or deleted or the enzyme concentration can be lowered or raised; a specific co-factor of an enzyme can be added or deleted or the concentration of the co-factor can be lowered or raised; a specific inhibitor of an enzyme can be added or deleted or the concentration of the inhibitor can be lowered or raised; a sample can be diluted or concentrated prior to, during or after exposure to a microcantilever; a sample can experience a temperature change prior to, during or after exposure to a microcantilever; a sample can experience a change in pH prior to, during or after exposure to a microcantilever; a sample can experience a change in conductivity prior to, during or after exposure to a microcantilever; and a sample can experience a change in viscosity prior to, during or after exposure to a microcantilever.

Measuring a deflection is measuring the distance moved or change in position of a microcantilever that alters from a first occupied position, at which first position the microcantilever with the biomaterial on the first surface of the microcantilever has not yet bound or reacted with the enzyme, to a second position occupied by the microcantilever after it has altered its position because of binding to or reaction of the biomaterial on the microcantilever with the enzyme in the environment, and consequent alteration of the biomaterial.

A deflection characteristic is a pattern of deflection of a microcantilever which is reproducible in extent of distance traveled, for example as measured in nm, and frequency per unit time. The deflection characteristic can distinguish specific conditions of enzyme and substrate, and further reaction conditions such as temperature, concentration, ionic strength, presence of an ion or other co-factor, presence of a preservative such as a protease inhibitor, and other conditions cell-known to one of skill in the enzymological arts. The extent of a deflection under a particular set of these conditions can become a signature for a specific reaction. A deflection characteristic is calculated from a measurement of extent of movement of the microcantilever, as a function of the time of addition of a sample, or as an extent of the movement as a function of concentration of an enzyme, of concentration of a substrate, of concentration of an inhibitor, of concentration of a co-factor, of pH, or of temperature, and the like.

A microprocessor can be included in an apparatus or a method, such as an integrated circuit containing the arithmetic, logic, and control circuitry required to interpret and execute instructions from a computer program. The microprocessor components of the measuring devices reside in an apparatus for detection of microcantilever deflection.

Detection of an Enzyme Substrate, Effector, or Associating Substance in an Environment The term "environment" means the entire set of factors to which a microcantilever is exposed for any given sample. For example, the set of factors may include the presence in the sample of a substance such as: a substantially purified enzyme; entire contents of a bodily fluid including at least one enzyme; a substantially pure inhibitor or other effector or associating substance; a bodily fluid or other biological mixture comprising an inhibitor inhibitor or other effector or associating substance, or combinations of such components. The term "environment" refers also to variable parameters such as the concentration of components of the sample that can affect enzyme activity. Factors such as temperature of the environment, while contributing to stress, are controlled by standard means well known to one of ordinary skill in the art, such as use of an insulated and thermally controllable housing, use of such housing in conjunction with a microfluidics device, and by monitoring of deflection of a reference microcantilever in an environment designed to omit any of the components in the reaction such as substrate, enzyme, or essential co-factor.

The reference microcantilever may be exposed to inactivated enzyme, for example, enzyme that is mutationally inactivated, or inactivated by heat or heavy metal binding which can serve as a negative control, and another reference microcantilever may be exposed to active enzyme to serve as a reference control to be compared to that found in the sample. The difference between the environments of the reference microcantilever and the experimental microcantilever results in a measure of the amount of deflection experienced by the experimental microcantilevers compared to the deflection seen in the reference environment as the background against which microcantilever deflections in the sample interaction cells are measured.

As used herein, deflection of a microcantilever from a first position to at least a second position as illustrated in FIG. 3 can occur by a physical or chemical alteration of an enzyme substrate molecule linked to a surface of a microcantilever. For example, a physical alteration which is a change in mass of the sensor material, e.g., of a substrate molecule, can occur when a DNA substrate reacts with either a DNA nuclease, such as an endonuclease or an exonuclease as a first exemplary case, or with a DNA ligase as a second exemplary case. In the first case, the alteration of the biomaterial on the microcantilever as a result of enzymatic activity is a reduction in molecular weight, which can cause a change in surface stress of the microcantilever and alter the position of the microcantilever, i.e., produce a deflection. In the second case, the alteration of biomaterial on the microcantilever is increase in molecular weight as a result of enzymatic activity, here too changing the surface stress, however in a manner that is directionally opposite from the deflection of the microcantilever in the first case. An initial deflection of the microcantilever occurs also when an associating substance such as an enzyme, for example, a nuclease molecule, binds to the DNA molecule. Further in time, digestion of the substrate and release or removal of the enzyme occurs, and deflection of the microcantilever to yet another position can be observed.

Similarly, deflection of the microcantilever can change from a first position to a second position due to a change in mechanical stress from additional presence on the surface when a substrate interacts with and binds the enzyme. Deflection can change from a second position to at least a third position, following, for example, activity of a ligase molecule that results in addition of a length of DNA to the DNA substrate molecule. Deflection can change from a third position to at least a fourth position when the ligase dissociates from the DNA substrate.

Another embodiment of a deflection of a microcantilever is observed when, for example, a physical alteration of a substrate molecule occurs when a DNA substrate reacts with a DNA endonuclease or exonuclease. Deflection of the microcantilever can change from a first position to at least a second position due to the increased weight on the surface when the substrate interacts with the enzyme. Deflection can change from a second position to at least a third position when the nuclease removes DNA from the DNA substrate molecule. Deflection can change from a third position to at least a fourth position when the nuclease disassociates from the DNA substrate. However, as these interactions occur at nsec to μsec speeds, real time monitoring of deflection is a measurement of an overall change in the substrate due to the enzymatic activity of the enzyme.

The deflection of a microcantilever can be measured by a means that is capacitive, piezoelectric, piezoresistive, or optical. The term "capacitive" means storage of energy in a non-conducting material resulting from a force or stress on the surface of the material. This force or stress can result in a deflection of the microcantilever. The term "piezoelectric" means a voltage and/or current produced between surfaces of a solid non-conducting material when a mechanical stress is applied to it. The term "piezoresistive" means a change in electrical resistance of a substance when a pressure or force is exerted on the surface of the substance. Optical means include use of ambient light and other sources of light, including lasers. Detection of microcantilever deflection by optical, electrical and mechanical means is shown in U.S. Pat. No. 5,653,939 issued Aug. 5, 1997. Use of laser light sources is shown in U.S. Pat. Nos. 6,016,686 issued Jan. 25, 2000, and 6,123,819, issued Sep. 26, 2000. Majumdar et al. (WO 01/14823 A1 international publication date Mar. 1, 2001) uses measurement of defraction of incident light to measure microforces with a set of microcantilever finger array blocks that can deflect relative to a set of fixed frame fingers. A device for illuminating each of a plurality of microcantilevers and measuring deflection by a change in angle of reflected light is the PV200 (Protiveris, Inc., Rockville, Md.; see Gen. Engin. News 23 (1), Jan. 1, 2003). Magnetic and electrical means for detection of deflection are shown in U.S. Pat. Nos. 5,807,758 issued Sep. 15, 1998, 5,156,810 issued Oct. 20, 1992, and in U.S. Pat. Nos. 5,981,297, issued Nov. 9, 1999, and 6,107,000 issued Aug. 22, 2000, respectively. Piezoelectric means for measuring deflection are shown in U.S. Pat. Nos. 5,814,525 issued Sep. 29, 1998; 5,445,008 issued Aug. 29, 1995; and 5,719,324, issued Feb. 17, 1998, respectively.

A time parameter is a time interval for measuring an event or an occurrence from a first point of time to at least a second point of time, and also a third, a fourth, etc., points in time. In general, the first point in time is noted as the time of exposing the microcantilever to the sample.

A stress is a force exerted on a surface of a microcantilever which can be associated with intermolecular interactions on that surface, such as: enzymatic alteration of a substrate on a first surface of a microcantilever, followed by enzyme release; or, irreversible binding of a protein in a sample to the substrate. Stress includes any type of force exerted on a surface of a microcantilever resulting from the interaction of a specific enzyme substrate, or a specific enzyme inhibitor, or a potential substrate, with an enzyme. Microcantilevers are sensitive to stress differentials due to different extents of interaction of a component of a sample, with one or more materials that have been further added to a coating layer on top of a first material.

The term "responsive" means that the microcantilever, including all coatings and sensor materials such as a substrate for an enzyme, is can deflect as a result of the stress generated by an interaction force that arises when an enzyme specifically interacts with the substrate. The resulting force may comprise chemical-mechanical forces, thermomechanical forces, electrostatic forces, magnetic forces, and other types of forces, alone or in combination.

Detection of an Associating Substance such as an Enzymatic Substrate or an Enzyme Effector in an Environment In addition to the embodiments described supra, microcantilever apparatuses and methods herein can be used to detect an enzyme substrate, an enzyme effector, or an enzyme associating substance in an environment that can bind to an enzyme, or can affect an enzyme activity. To configure use of the microcantilever to detect an enzymatic substrate or effector in a sample from the environment, for example, in a biological sample, the enzyme is immobilized to one surface of the microcantilever, for example, using the cross-linkers as described herein.

A microcantilever produced in this manner can be used to detect a substrate, or an effector of the enzyme, or an associating substance for the enzyme, when exposed to an environmental sample such as a sample of biological fluid. Binding of the substrate, effector, or associating substance to the enzyme, which is immobilized on one surface of the microcantilever, will alter the surface tension and thereby produce a deflection of the microcantilever as in FIG. 3. As a function of time of the assay, the extent and direction of further deflection will be altered as a result of enzymatic activity of the immobilized enzyme acting on bound substrate. Along the entire surface of the microcantilever, a plurality of enzyme molecules are immobilized, each of which can bind and release a number of substrate, effector, or associating substance molecules during a brief incubation period of several seconds to several minutes duration, an effective extent of deflection will be a comparatively continuous function, readily distinguishable in comparison to a control microcantilever. A control microcantilever is, for example, is identically prepared with respect to the enzyme but not exposed to the sample containing the substrate, effector, or associating substance. Alternatively, a control microcantilever is, for example, is identically prepared but lacking the enzyme, or prepared with denatured enzyme, and is exposed to the sample containing the substrate, effector, or associating substance.

One of ordinary skill in the art of enzymology can further arrange to withhold or delay additional of a component that is required for enzymatic activity, such as a bivalent cation. Alternatively, one can add an enzyme inhibitor to the sample buffer, simultaneous to addition of the sample, or after addition of the sample, such as a chelator for a bivalent cation (e.g., addition of the chelator EDTA, or EGTA simultaneous to or after addition of the sample containing the substrate).

The term "inhibitor" as used herein means a composition that substantially reduces measurable enzyme activity, for example, by at least about two-fold, about four-fold, or at least by about ten-fold. Reduction in enzyme activity can result either from decreased affinity of the enzyme for a substrate, for example, by a competitive occupancy of the active site of the enzyme, or from decreased turnover rate by the enzyme of the substrate converted into a product and released. An inhibitor can be a low molecular weight compound, as defined herein, or it can be a macromolecular substance, such as an inhibitory protein.

An "effector" can be any substance that alters an enzyme activity, for example, that changes the substrate specificity by a steric mechanism, or that activates or inhibits the activity with the conventional substrate. An "associating substance" can be any material that binds to the enzyme or the enzymatic substrate, such as an antibody, a binding protein, or derivative of a substrate such as a pseudosubstrate that is bound to the enzyme at the active site but not acted upon enzymatically, for example, is not cleaved. Non-limiting examples of associating substances include: an inactive enzyme which is an associating substance for a substrate immobilized on a microcantilever; a pseudosubstrate which is an associating substance for an enzyme immobilized on a microcantilever.

Use of such variables as time, absence of a cofactor required for activity followed by or compared to addition of the cofactor, addition of an enzyme inhibitor such as trypsin inhibitor aprotinin (molecular weight about 6,000 daltons), and use of a competitive pseudo-substrate or an active site poison and can provide additional confirmatory data concerning the identity of the component of the sample as a substrate, an effector, or an associating substance of the enzyme on the microcantilever.

Enzymes

The term "enzyme" encompasses a large number of protein biological catalysts, which are known to or are predicted to catalyze a reaction. Most commonly, an enzyme can catalyze at least one of many different possible biochemical reactions that comprise biological pathways. Further, an enzyme can catalyze an organic chemical reaction, such as conversion of ethanol to acetic acid, or an inorganic reaction, such as reduction of molecular nitrogen.

The molecules that are the results of an enzymatically catalyzed reaction are referred to as "products." The terms enzyme, substrate, and product are standard terms in the arts of enzymology and biochemistry. The term enzyme can include, for example, an active enzyme in a sample capable of modifying its enzymatic substrate to yield an enzymatic product on a microcantilever; a genetically altered enzyme having a catalytic defect; an enzyme lacking a cofactor essential for catalytic activity; and an enzyme in a sample binding irreversibly to a pseudosubstrate. The interaction forces generated by enzyme activity on a substrate molecule may comprise chemical-mechanical forces, thermal-mechanical forces, electrostatic forces, magnetic forces, and other types of forces.

Enzymes encompass six general classes based on the reaction being catalyzed, including: isomerases, oxidoreductases, transferases, hydrolases, lyases, and ligases. Isomerases catalyze the conversion of a substrate which is a chemical compound, to a different chemical compound product that contains the same number and type of atoms, but in a different structural configuration. Oxidoreductases are involved in oxidation, reduction, and electron or proton transfer reactions of the substrate. Transferases catalyze reactions in which groups of atoms are transferred to or from substrate molecules. Hydrolases cleave one or more of a variety of covalent bonds of the substrate by hydrolysis. Ligases join two or more substrate components to form a covalent bond, each component being part of a substrate complex. Enzymes that are known in the art can be purified from cells that have been collected and concentrated as the enzymes are thus purified. Cells are ruptured by methods commonly employed by artisans in microbiology and cell biology, for example, sonication, French press, freeze thawing, and detergent lysis.

Secreted microbial enzymes can be obtained from spent culture medium, i.e., growth medium from which cells have been removed following culture and growth of cells. Enzymes can be purified by procedures including column chromatography, particularly affinity column chromatography, and also ion-exchange column chromatography, size exclusion column chromatography, and, as fusion proteins, can be purified using highly specific affinity ligands (see New England Biolabs Catalog, 2000–2001, pp. 142–143).

Enzymes are purified and stored in suitable buffers containing anti-oxidant agents, such as dithiothreitol or mercaptoethanol, to maintain native cysteine disulfide bonds in a reduced condition, and with chelators such as EDTA to protect the enzyme from heavy metal inactivation. Enzymes can be stored at −20° C. or −70° C., with an agent such as glycerol or DMSO to prevent water crystal formation, or in a suitable buffer. Many enzymes of interest are commercially available (Sigma Aldrich, Inc., St. Louis, Mo.; Calbiochem, San Diego, Calif.; New England Biolabs, Inc. Beverly, Mass.), as are suitable buffers for storage and concentrated reaction mixes that are formulated for optimal enzyme activity and include appropriate ions. Alternatively, enzymes are available as purified crystals, which can be dissolved in a suitable buffer at a specific appropriate concentration prior to use.

Enzymes herein include in scope any genetically engineered or semi-synthetic peptide-containing molecule capable of reacting with another molecule to promote a chemical change, for example, a catalytic antibody. The term enzyme is further envisioned to include an activity that has not yet been characterized, but for which a substrate and assay system can be devised, for example, a DNA restriction endonuclease that recognizes and binds to a palindromic or non-palindromic sequence consisting of 10 or more nucleotides. Further, the term enzyme includes naturally-occuring or genetically engineered derivatives of an enzyme with known activity, including a derivative having reduced or essentially no activity.

Enzymes having a known activity are characterized using the methods and apparatuses herein by parameters of that activity associated with a particular enzymatic substrate, including affinity for the substrate, and rate of turnover of the substrate to yield product. The parameters of $K_m$ (Michaelis constant) as a measure of affinity for a substrate, and $V_{max}$, which as a maximum velocity, are well known to one of ordinary skill in the art of enzymology. These parameters are determined by analyses of enzyme activity as a function of concentrations of enzyme and substrate, and by observing the reaction as a function of time. Mutated enzymes, and active enzymes in the presence of an enzyme inhibitor, can exhibit a lower affinity for a particular substrate (increased $K_m$) or a lower turnover number (decreased $V_{max}$). The methods and apparatuses of the present invention can be optimized to determine control values, and subsequent changes, in $K_m$ and $V_{max}$ values of enzymes that are mutated, or are in the presence of an inhibitor, as defined herein, or in the presence of substrate analogs, derivatives, or pseudosubstrates, and for identification and analysis of enzyme inhibitors.

Substrates for Enzymatic Activity

The term "substrate" as used in this description and in the claims means a molecule specifically chosen by one of ordinary skill in the biochemistry of enzymes, because it is known to be a substance that reacts with an enzyme of interest. The molecule of substrate, or mixture of different molecules of different substrates, can be chosen because at least one of the types of molecules is known to bind specifically to the active site of the enzyme, such that the enzyme acts to catalyze a chemical reaction that alters the substrate. For example, the substrate can be a particular protein for an enzyme which is protease; or, the substrate can be a DNA molecule having a particular nucleotide sequence that can be recognized by a molecule of a restriction endonuclease.

A substrate can be designed to detect a novel enzymatic activity, i.e., an enzymatic activity that might be present but is not currently known to be present in one of a plurality of natural product samples, or from a library of mutated enzymes. The term "substrate" is commonly used in the engineering arts to indicate a surface which acts as a support for another material, for example, in U.S. Pat. No. 6,123, 819, issued Sep. 26, 2000. In the present application the term "substrate" is used to refer only to a member of that particular class of molecule which specifically can interact with an enzyme of choice, and which can be bound by the enzyme and be further chemically altered by a reaction catalyzed by the enzyme, to yield a product that is chemically different from the initial substrate material.

Substrates need not be the natural substrate of an enzyme, and can be designed according to the particular purpose of the user, including diagnostics, inhibitor search, purity monitoring, or novel enzyme discovery. Substrates can be nature-identifical, e.g., a protein in a native configuration, or can be denatured and further chemically modified. The substrate can also be further modified for use with other means of detection, for example, a substrate can be colorigenic, fluorogenic, or radioactive, although these modifications need not affect an aspect of microcantilever deflection.

Under some circumstances it is desirable to have a dense array of substrate molecules, for example, short substrate molecules, as opposed to a less dense array of longer substrate molecules. The kinetics of enzyme digestion of a substrate on a surface of a microcantilever can depend on the size of the particular enzyme, for example, the Stokes radius of the enzyme, so that an optimal extent of density and size of substrate molecules should be determined by the user experimentally. The density of the substrate on the first surface of the microcantilever can be adjusted by varying one or more of the factors, including the concentration of the enzyme, the temperature of the reaction of enzyme with cross-linking agent, or the duration of time of this reaction. Further, the substrate can be a mixture of suitable molecules, as can be determined by one of skill in the art of enzymology.

A sensor material can be deposited on the surface of a microcantilever, and can interact with a component of a sample, for example, the sensor material is a biomaterial. In another embodiment, the sensor material can be any substance with which a protein, particularly an enzyme can interact, and which can be immobilized on microcantilever.

The term "biomaterial" means any organic material isolated from a natural source, or produced synthetically, or produced semi-synthetically by chemical synthesis with an organic starting material. For example, a biomaterial can be isolated from a natural source such as an animal tissue, a plant, or from bacterial cells, using technology cell known to one skilled in the art. A biomaterial such as a protein can be synthesized semi-synthetically using recombinant DNA technology, or in a eukaryotic cell-free system, by methods which are cell known to one skilled in the art. A protein can also be synthesized de novo using solid state or solution peptide synthesis chemistry, with commercially available devices and substrates cell known to one skilled in the art of peptide synthesis. A biomaterial can be all or a portion of a cell. A sensor for the detection of bound *E. coli* cells immobilized using antibodies on microfabricated structures is disclosed in Ilic et al. "Mechanical resonant immunospecific biological detector", Appl. Phys. Lett. Vol. 77, No. 3, pgs. 450–452, Jul. 17, 2000. Biomaterials and other sensor materials can be obtained commercially, or can be produced by the artisan in the laboratory.

The phrase "non-cleavable pseudosubstrate" means a molecule that is chemically similar to a natural substrate of the enzyme, which can bind the enzyme, but which pseudosubstrate is not altered chemically. A pseudosubstrate can bind covalently or non-covalently to the enzyme active site, but cannot be converted to the end product of the chemical reaction. For example, a proteinaceous protease inhibitor can act as a pseudosubstrate for a protease, for example, a synthetic inhibitor can act as a pseudosubstrate for a cAMP-dependent protein kinase.

The phrase "substantially pure" means that the enzyme of interest has been physically manipulated to increase the final concentration in comparison to the initial concentration, with respect to other non-enzyme materials, for example, so that the enzyme solution is at least 80% pure, is at least 90% pure, is at least 95% pure, or is at least 99% pure with respect to non-enzyme components of the solution.

It is well-known in the pharmacological arts that for an enzyme associated with a disease condition, such as a cancer, a cardia condition, a clotting disorder, or the presence of a pathogen, an enzyme inhibitor can be a potential therapeutic agent.

Samples

The term "sample" means the components dissolved or dispersed in a fluid state. A sample of interest can be assayed for the presence of a diagnostically important enzyme in a sample from a subject; alternatively, a sample can be assayed for presence of a novel enzyme activity.

The term "bodily fluid" means any fluid produced or secreted within or by a body of an animal, blood, lymph, tissue fluid, urine, bile, sweat, synovial fluid, amniotic fluid, abdominal fluid, pericardial fluid, pleural fluid, cerebrospinal fluid, gastric juice, intestinal juice, joint cavity fluid, tears, and nasal discharge.

The phrase "medical condition" means any condition in which the health of a subject is impaired. The medical condition can include for example a genetic defect, an infection, a cancer which can be a leukemia or a tumor, and the like.

The term "infection" is meant to include disorders of a human or animal subject caused by one or more species of bacteria, viruses, fungi, or protozoans, which are disease-producing organisms collectively referred to as "pathogens." The term "fungi" is meant to include the yeasts. In this invention, pathogens are exemplified by, but not limited to: Gram-positive bacteria such as *Bacillus anthracis, Enterococcus fecalis, Hemophilus pneumoniae, Listeria monocytogenes, Mycobacterium tuberculosis, M. leprae, Proprionibacterium acnes, Staphylococcus aureus, S. epidermis, S. intermedias, Streptococcus hemolyticus, S. pneumoniae;* Gram-negative bacteria such as *Flavobacterium meningosepticum, Helicobacter pylori, Hemophilus pneumoniae, H. influenzae, Klebsiella pneumonia, Neisseria gonorrhoeae, Pseudomonas aeruginosa, Shigella dysenteria, Salmonella typhi, S. paratyphi, Escherichia coli* serotype 0157:H7, *Chlamydia* species; viruses such as HIV-1, -2, and -3, HSV-I and -II, non-A non-B non-C hepatitis virus, Newcastle disease virus, rabies virus, Herpes simplex viruses type I and type II, and pox viruses such as smallpox; fungi such as *Candida albicans, C. tropicalis, C. krusei, C. pseudotropicalis, C. parapsilosis, C. quillermondii, C. stellatoidea, Aspergillus fumigatus, A. niger, A. nidulans, A. flavus, A. terreus, Absidia corymbifera, A. ramosa, Cryptococcus neoforms, Histoplasma capsulatum, Coccidioides immitis, Pneumocystis carinii, Rhizopus arrhizus, R. oryzae, Mucor pusillus* and other fungi; and protozoa such as *Entamoeba histolytica, Entamoeba coli, Giardia lamblia, G. intestinalis,* Eimeria sp., Toxoplasma sp., *Cryptosporidium parvum, C. muris, C. baileyi, C. meleagridis, C. wrairi,* and *C. nosarum.* Obtaining unique epitopes from these organisms by screening proteins and by assaying peptides in vitro are commonly known to those skilled in the art.

The phrase "genetic defect" means any inheritable pathological condition which is caused by the presence of a mutant allele or disease gene. Examples include but are not limited to: Fabry disease, Gaucher disease, Tay-Sachs disease, Lesch-Nyhan disease, mannosidosis disease, celiac disease, X-linked glomerular disease, and mucopolysaccharidosis.

Cross-Linking Agents

The term "attachment" with respect to an enzymatic substrate and a first surface of a microcantilever, means a covalently bonded or other physically connected molecule of substrate that is connected to the coating material on the first surface of the microcantilever. In a preferred embodiment, an attachment is a covalent bond from the substrate to an atom of a chemical linker, e.g., a bifunctional cross-linking reagent or "cross-linker", which is also covalently bonded through a different atom to the first surface. Attachment can also be by direct non-covalent connection of the biomaterial to the coating material on the first surface without modification of either the first surface or the biomolecule. Such connection can be due to complementarity of shape, charge, and/or to exclusion of waters of hydration, hydrophobicity, or other characteristics of the particular combination of the first surface and the particular substrate (U.S. Pat. No. 6,123,819, issued Sep. 26, 2000).

The phrase "bifunctional cross-linker" means a substance which can connect a first component to a second component, wherein the cross-linker consists of a carbon chain and has a first chemically reactive group at a first end of the substance and a second bioreactive group at a second end of the substance. A chemical reaction between the first end of the substance with a first component, and a chemical reaction between the second end of the substance with a second component, results in the linkage of the first and second components of the invention herein. A bifunctional cross-linker is used to bind a substrate molecule to a first surface of a microcantilever, for example, to bind a protein substrate such as a collagen to a first surface having a gold coating.

For example, bifunctional cross-linkers can include the following compounds: dithiobis(succinimidyl-undecanoate) (DSU), and can be purchased from Pierce Endogen, Inc. (Rockford, Ill.); long chain succinimido-6-[3-(2-pyridyldithio)-propionamido] hexanoate (LCSPDP), contains pyridyldithio and NHS ester reactive groups which react with sulfhydryl and amino groups, can be purchased from Pierce; succinimidyl-6-[3-(2-pyridyldithio)-propionamido] hexanoate (SPDP) contains pyridyldithio and NHS ester reactive groups which react with sulfhydryl and amino groups, can be purchased from Pierce (Rockford, Ill.); and m-maleimidobenzoyl-N-hydroxysuccinimide ester (MBS) contains NHS ester and maleimide reactive groups which react with amino and sulhydryl groups, and can be purchased from Pierce (Rockford, Ill.).

The methods of the present invention include screening of chemical compositions as potential drugs. Libraries of chemical compositions can be obtained commercially, custom made or available in stock, for example, from ChemBridge (San Diego, Calif.) and from PharmaCore (High Point, N.C.) or from the NIH. Alternatively, libraries chemical can be synthesized according to any of a variety of methods, for example, see U.S. Pat. Nos. 6,377,895 issued Apr. 23, 2002, and 5,908,960 issued Jun. 1, 1999.

The terms "protein", "polypeptide", and "peptide", as used herein, shall have the same meaning.

The above embodiments of the invention, having been fully described, are illustrated by the following Examples and claims, which are not intended to be further limiting. The contents of all cited references are hereby incorporated by reference herein.

EXAMPLES

Example 1

Papain Digestion of an Immunoglobin IgG Antibody Substrate

A surface having a gold-coated microcantilever was cleaned by exposure to an ozone-enriched atmosphere for 10 min. The cross-linking agent was attached by immersing the microcantilever in a solution of 0.1% (w/v) DSU in dioxane for 60 min. The microcantilever was washed three times with dioxane, followed by a wash with phosphate buffered saline (PBS), pH 7.6.

The microcantilever was further incubated with a solution of Immunoglobulin G (1 mg/mL; CalBiochem, San Diego, Calif.) in PBS solution for 60 min, to covalently attach a protein substrate for the enzyme papain to the coated first surface of the microcantilever. The microcantilever was removed from the antibody solution and immersed in a carbonate buffer solution, pH 8.5, for 30 min to hydrolyze any unreacted DSU.

The microcantilever was mounted in a cell of an atomic force microscope (AFM), and measurement of microcantilever deflection was initiated. After attainment of a stable baseline, a 100 microliter sample of a PBS solution containing a 0.1% (w/v) solution of the detergent Tween was injected into the cell. Microcantilever deflection was monitored as a function of time, as is depicted in FIG. 4 as "control." Next, a 100 microliter sample of papain (100 micrograms per mL; CalBiochem, San Diego, Calif.) was injected into the cell. Microcantilever deflection was monitored as a function of time, and the results are depicted in FIG. 4, labeled as "papain."

The steady upward bending of the microcantilever shown in FIG. 4 denotes loss of mass of the protein substrate from the gold-coated first surface of the microcantilever. The data shown are one example of several observations, having the same result. The data show monitoring of enzymatic activity of papain as a function of time. Further, these data show the capability of the microcantilever to measure enzymatic activity.

Example 2

Neisseria Secreted Protease Digestion of IgG Substrate

A surface having a gold-coated microcantilever is cleaned by exposure to an ozone-enriched atmosphere for 10 min. The cross-linking agent is attached by immersing the microcantilever in a solution of 0.1% (w/v) DSU in dioxane for 60 min. The microcantilever is washed with dioxane, followed by a wash with phosphate buffered saline (PBS), pH 7.6.

The microcantilever is further incubated with a solution of Immunoglobulin G (1 mg/mL; CalBiochem, San Diego, Calif.) in PBS solution for 60 min to covalently attach the IgG protein substrate to the surface. The microcantilever is removed from the antibody solution and immersed in a carbonate buffer solution, pH 8.5, for 30 min to hydrolyze any unreacted DSU.

The microcantilever is mounted in a cell of an AFM and measurement of deflection is initiated. After attainment of a stable baseline, a 100 microliter aliquot of a PBS solution containing 0.1% (w/v) solution of the detergent Tween is injected into the cell. Microcantilever deflection is monitored as a function of time. Next, a 100 microliter aliquot of a sample containing a Neisseria secreted protease is injected into the cell. Microcantilever deflection is further monitored as a function of time.

The steady upward bending of the microcantilever indicates loss of mass of the protein substrate from the gold-coated side of the microcantilever. Many other bacterial pathogens secrete a similar antibody-specific proteolytic enzyme during a course of pathogenesis, which enzyme can be detected by use of a microcantilever.

Example 3

Screening Samples for an Inhibitor to a Matrix Metalloprotease

A variety of enzymes have been associated with pathologies, for example, appearances of certain metalloproteinases known as metalloproteinase type IV collagenase and gelatinase A, which in normal subjects are expressed only during embryo implantation, are associated with a number of pathological conditions, including cancer metastasis and angiogenesis. Analysis of samples for ppresence of potential inhibitors, using known inhibitors as positive controls (U.S. Pat. Nos. 5,643,908 and 6,037,361), can be achieved using the microcantilevers produced as in methods herein, with the metalloproteinase molecules attached to a surface of the microcantilevers.

Gelatinase A is immobilized on a set of microcantilevers (microcantilever chip) using the cross-linking agent as described in Example 1, supra, the chip located in an interaction cell in a microfluidics device. A sample containing soluble gelatin is introduced into the interaction cell, and deflection of the microcantilevers is recorded. Candidate inhibitory molecules are introduced, one at a time or in a plurality, such as "sibling" groups of 10 or more, into the interaction cell. A control lacking any inhibitory candidates is maintained as a reference cell.

The presence of a gelatinase inhibitor is noted as a change in deflection of the microcantilevers, for example, a decrease in deflection of the microcantilevers.

Further analysis comprises identification of the inhibitor, for example if in the presence of a sibling group of compounds, testing of fewer siblings or each compound individually, and then testing of the active compound as a function of concentration, using multiple cells of a microfluidics device. In this manner, an inhibitor of the gelatinase is identified, and kinetic parameters of inhibition of gelatinase enzyme activity are determined.

What is claimed is:

1. A method for identifying an inhibitor of an enzyme from among a plurality of potential inhibitors of binding of the enzyme to a substrate, the method comprising:
   adding a sample of one of the potential inhibitors with the substrate to a first interaction chamber in a microfluidics apparatus having a plurality of chambers, wherein each chamber contains a block array having a plurality of identically configured microcantilevers, the first interaction chamber containing the enzyme bound to a surface of a first block array comprising a plurality of first microcantilevers; and,
   comparing a deflection of each of the plurality of the first microcantilevers in the first interaction chamber to that of a each of a second block array comprising a plurality of second microcantilevers in a second interaction chamber, wherein the first and second microcantilevers are identically configured with the enzyme bound to the surface, and the first and second interaction chambers are identically configured to contain the substrate, with the exception that the second chamber does not receive a sample of an potential inhibitor, and further comparing the deflection of each of the first and second block arrars comprising a plurality of third microcantilever in a third interaction chamber, wherein the third interaction chamber receives an inhibitor that is a positive control, which inhibits binding of the substrate to the enzyme, or the third chamber receives a control baffer lacking the substrate, such the a decrease in the deflection of the first microcantilevers in comparison to the second microcantilever and to the third chamber lacking the substrate, is an indication that the inhibitor in the first chamber has been identified.

2. A method according to claim 1, wherein the substrate is a pseudosubstrate.

* * * * *

UNITED STATES PATENT AND TRADEMARK OFFICE
CERTIFICATE OF CORRECTION

| | | |
|---|---|---|
| PATENT NO. | : 7,141,385 B2 | Page 1 of 1 |
| APPLICATION NO. | : 10/346443 | |
| DATED | : November 28, 2006 | |
| INVENTOR(S) | : Bottomley et al. | |

It is certified that error appears in the above-identified patent and that said Letters Patent is hereby corrected as shown below:

Col. 22, Claim 1, Line 27: delete "the exception" and insert --an exception--

Col. 22, Claim 1, Line 28: delete "an potential" and insert --the potential--

Col. 22, Claim 1, Line 30: delete "arrars" and insert --arrays--

Col. 22, Claim 1, Line 30: delete "microcantilever" and insert --microcantilevers--

Col. 22, Claim 1, Line 34: delete "baffer" and insert --buffer--

Col. 22, Claim 1, Line 35: delete "such the a decrease" and insert --such that a decrease--

Col. 22, Claim 1, Line 37: delete "microcantilever" and insert --microcantilevers--

Signed and Sealed this

Sixth Day of February, 2007

JON W. DUDAS
*Director of the United States Patent and Trademark Office*